United States Patent [19]

Subramanian

[11] Patent Number: 4,666,843
[45] Date of Patent: May 19, 1987

[54] METHOD FOR THE PURIFICATION OF CALF RENNET

[75] Inventor: Sethuraman Subramanian, Elkhart, Ind.

[73] Assignee: Miles Laboratories, Inc., Elkhart, Ind.

[21] Appl. No.: 787,998

[22] Filed: Oct. 16, 1985

[51] Int. Cl.$^4$ .............................................. C12N 9/64
[52] U.S. Cl. .................................... 435/226; 435/815
[58] Field of Search ................................ 435/226, 815

[56] References Cited

PUBLICATIONS

Kobayashi et al, Agricultural and Biological Chemistry vol. 42, pp. 2227–2231 (1978).
Lowe et al in Methods in Enzymology, vol. 104, pp. 97–113 (1984).

Primary Examiner—Lionel M. Shapiro
Attorney, Agent, or Firm—Jerome L. Jeffers

[57] ABSTRACT

Disclosed is a method for the purification of calf rennet which involves contacting the rennet with an affinity ligand, e.g. Cibacron Blue, to cause separation of the chymosin and pepsin contained in the rennet.

11 Claims, 5 Drawing Figures

METHOD FOR THE PURIFICATION OF CALF RENNET

BACKGROUND OF THE INVENTION

Chymosin (EC 3.4.23.4) is the predominant milk-clotting enzyme in the fourth stomach of unweaned calves Use of this enzyme in cheese making has been known since ancient times.

Calf chymosin used for commercial cheese making is typically found in rennet, an impure extract leached from the calf stomach. In calf rennet, 5-20% of the milk clotting activity is due to bovine pepsin with the amount of pepsin in the rennet being a function of the age, weaning and diet of the calves whose stomachs are processed during its preparation. When mixtures of pepsin and chymosin are used to make cheddar cheese, higher levels of non-protein nitrogen and fat are found in the whey when rennet containing higher levels of pepsin is used. Although there is no significant difference in the composition, flavor or texture of the cheese made with differing pepsin contents, the yield is 0.25% lower with pure bovine pepsin than is the case with rennet, an economically significant difference. In addition, pepsin has greater proteolytic activity than chymosin at all pH values from 2 to 6. If the proteolytic activity is excessive, the yield of cheese and retention of fat by the curd may be diminished. Excessive proteolysis during ripening also has undesirable effects on the body and flavor of the finished cheese. For these reasons, it is desirable to use rennin having a reduced pepsin level in the manufacture of cheese. Bovine pepsin can be inactivated at an alkaline pH for example, by incubating at a pH of 7-7.3 for 30 minutes at 30° C. but not without inactivating some chymosin too. Because of the critical conditions necessary for the selective inactivation of pepsin, methods by which pepsin and chymosin are separated are to be preferred over the selective inactivation technique.

Garnot et al discuss the separation of chymosin from pepsin in calf rennet in *J. Dairy Science*, 55, 1641-1650 (1972). After exhaustive dialysis the sample is applied to a microgranular DEAE cellulose column. Both chymosin and pepsin are adsorbed on the column, however, application of a linear gradient of NaCl eluted chymosin first and pepsin at a higher salt concentration. This method was used primarily for the determination of the enzymatic composition of several commercial rennet preparations.

In *Anal. Biochem.*, 139, 265-271 (1984), Pohl et al disclose the preparation of an affinity ligand (a synthetic inhibitor of aspartate proteinases) and its attachment to Sepharose 4B, which is then used to purify bovine cathepsin D and also human, porcine and chicken pepsins. These enzymes bind to the support over the pH range of 2-5. A buffer at pH≧6, low ionic strength and containing 20% dioxane served as a general desorption agent. The peptide inhibitor (Sepharose) is a general purpose ligand which can bind most aspartate proteinases and is thus not discriminatory. Bovine Cathepsin D could be purified on the affinity column because the contaminant proteinases were all of the cysteine type (rather than aspartate proteinases) which did not bind to the column.

The use of pepstatin-Sepharose as the affinity medium for the purification of chymosin is disclosed in *Agric. Biol. Chem.*, 42, 2227-2231 (1978) by Kobayashi et al. This method results in poor recovery ($\approx 60\%$) and pepstatin is quite expensive for use in commercial scale operations.

Dean et al in *J. Chromatogr.*, 165, 301 (1979) and Burgett et al in *Am. Lab.*, p. 74 (1977) enumerate a large number of enzymes which have successfully been separated on a Cibacron Blue F3GA column. These enzymes include hexokinase, DNA-polymerase, alcohol dehydrogenase, adenylate kinase, ribonuclease, glyoxalase, cytochrome C, aldolase, blood clotting factor X and enolase. These enzymes do not have many features in common either in terms of structure or function.

SUMMARY OF THE INVENTION

The present invention is a method for the purification of calf rennet by separating pepsin therefrom. The method comprises contacting the rennet with an affinity ligand of the formula:

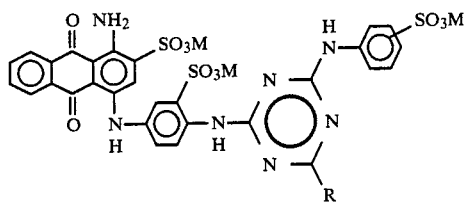

where R is a solubilizing moiety or a moiety which will insolubilize the ligand without affecting its affinity characteristics at a pH of from 5.4 to 5.7 to cause separation of chymosin and pepsin contained in the rennet.

The percentage figures on peaks A and B represent the integrated milk clotting activity under each peak.

Figure 1:
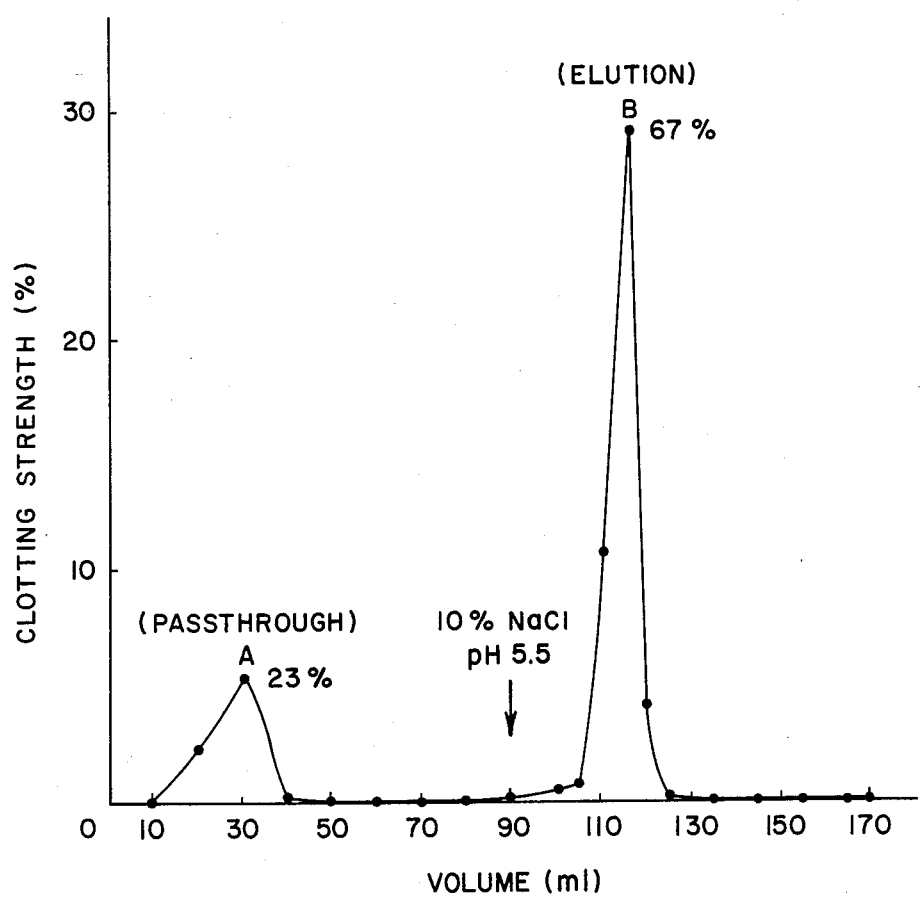
FIG. 1—Calf rennet dialyzed in 0.025 M sodium citrate at pH 5.5 was applied to a Blue agarose column (1.5 cm×10 cm) incubated with the same buffer, washed extensively and then eluted with 0.025 M citrate buffer (at pH 5.5) containing 10% NaCl. The pass-through fraction was >96% pepsin and the eluted peak was >96% chymosin.
Figure 2:
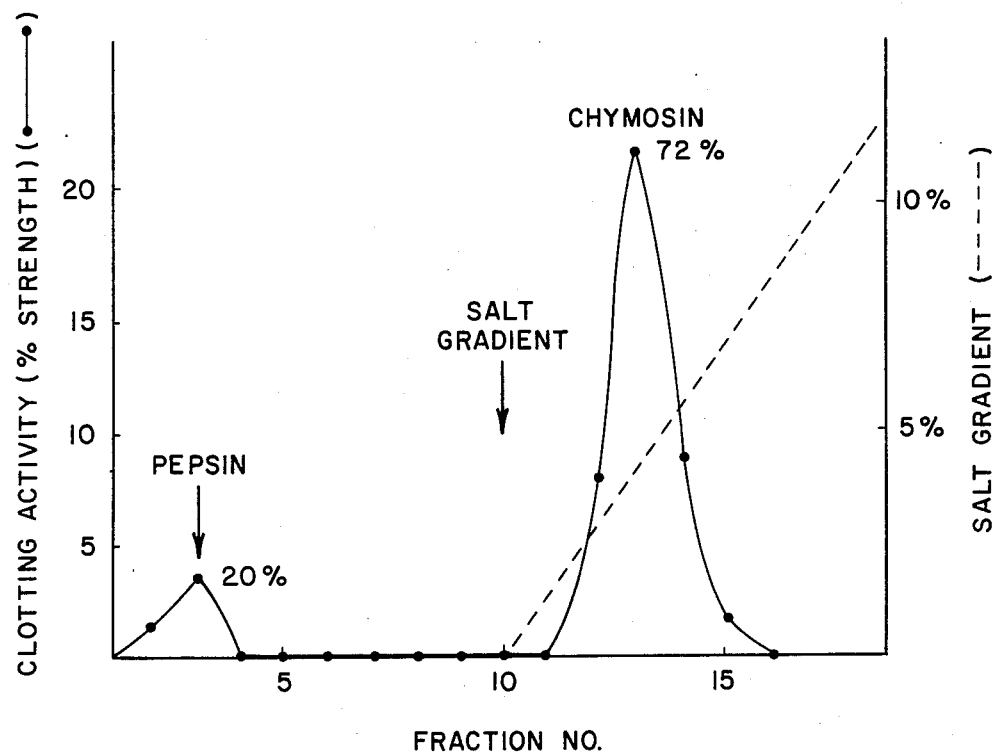

FIG. 2—Same conditions as in FIG. 1. Elution was effected by a 0-18% NaCl gradient. Pepsin passed through unadsorbed. Peak chymosin activity was eluted at 3.17% NaCl.

Figure 3:
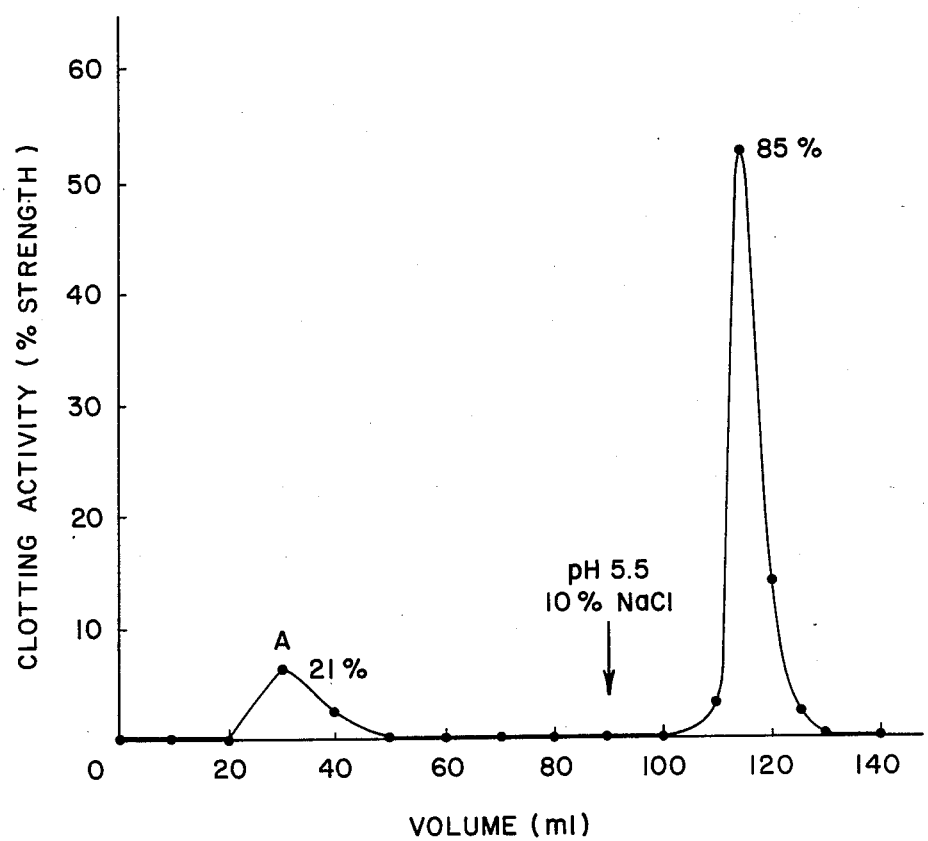

FIG. 3—Calf rennet was dialyzed in 0.025 M sodium citrate containing 0.75 M Na$_2$SO$_4$ at pH 5.5 and applied to the Blue agarose column incubated in the same buffer. After washing, the bound chymosin was eluted with 0.025 M citrate at pH 5.5 containing 10% NaCl. As before, peak A was pure pepsin; the eluted fraction was pure chymosin.

Figure 4:
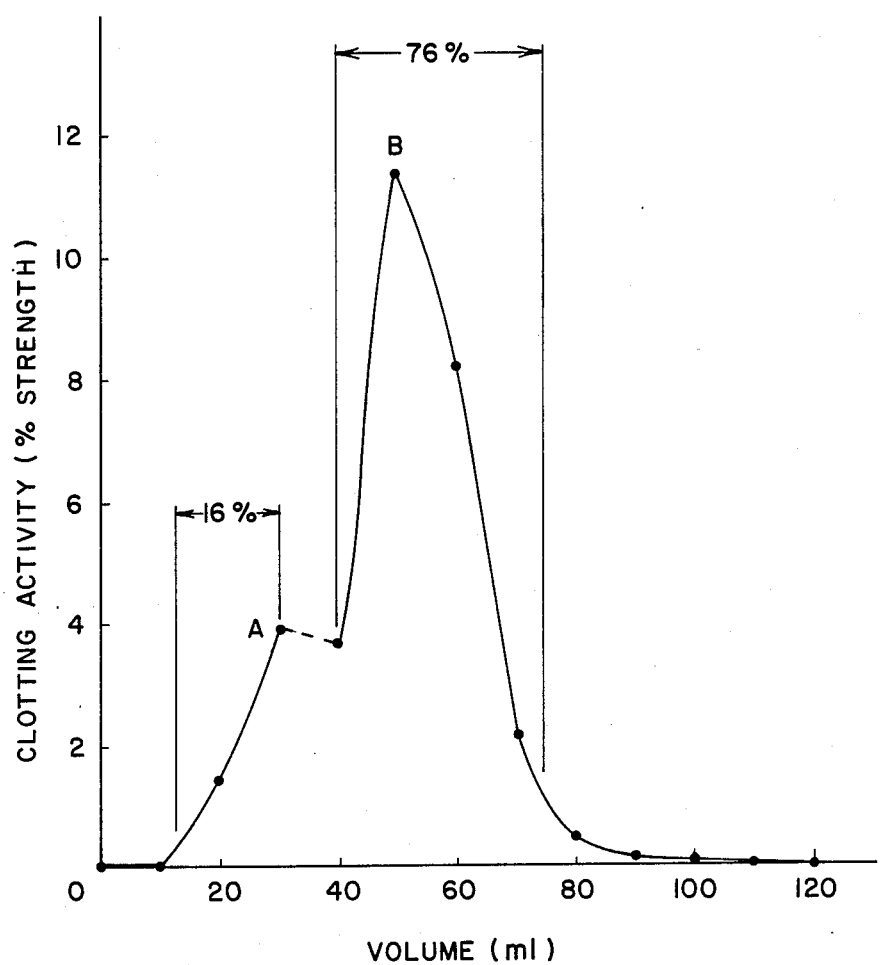

FIG. 4—Calf rennet dialyzed in 0.025 M sodium citrate buffer containing 0.5% NaCl (0.085 M) at pH 5.5 was applied to the Blue agarose column. Both pepsin and chymosin pass through unadsorbed except chymosin is retarded longer than pepsin.

The fraction corresponding to A is pure pepsin, and the following fractions are pure chymosin. The percentage figures refer to integrated clotting activity under each peak.

Figure 5:
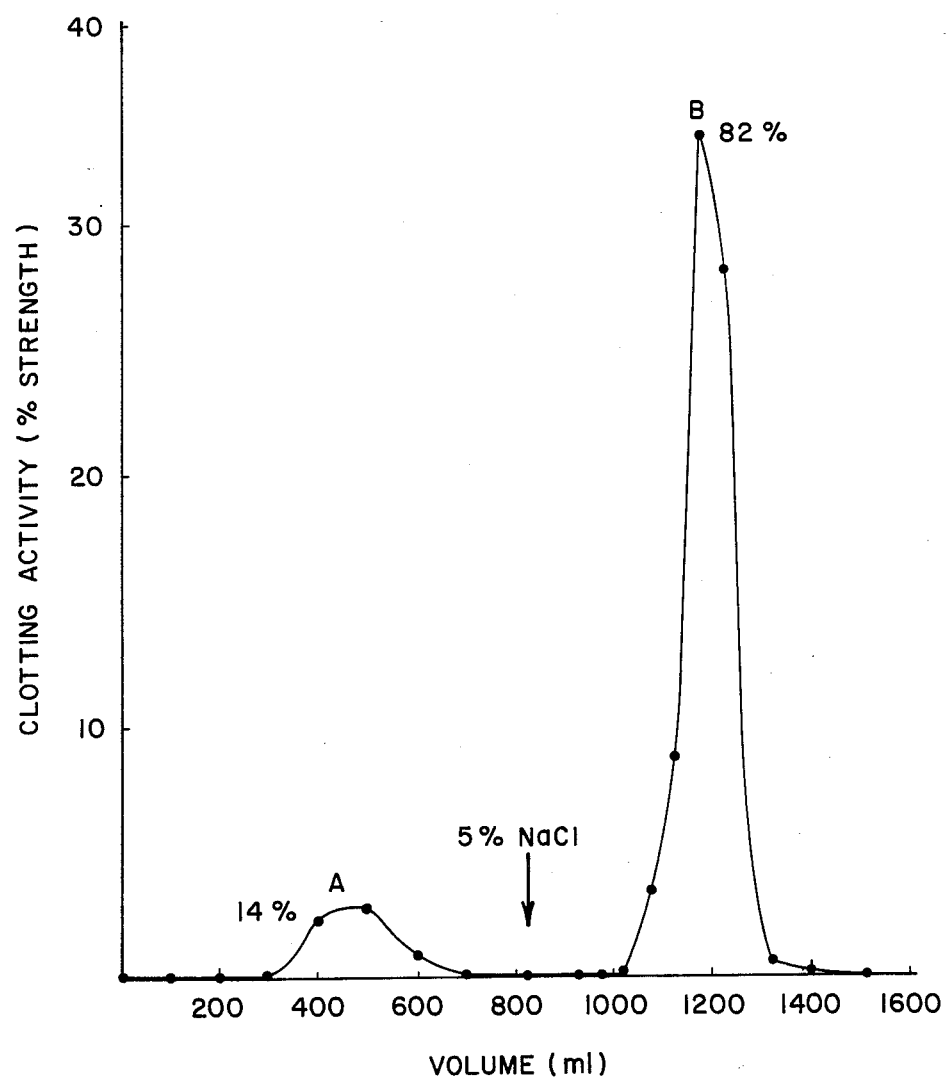

FIG. 5—A large scale isolation of chymosin and pepsin. Calf rennet was extracted from calf stomachs using 10% Na$_2$SO$_4$ (instead of NaCl). After contrifuging to remove debris, 470 ml of calf rennet ($\approx 11\%$ clotting activity) was ultrafiltered to about 250 ml and applied to a large Blue agarose column (6 cm×14 cm).

After washing, the bound chymosin was eluted with 0.025 M citrate containing 5% NaCl at pH 5.5.

DESCRIPTION OF THE INVENTION

The present technique is capable of separating pepsin from chymosin in calf rennet by selectively retaining or retarding chymosin on an affinity column under controlled conditions and letting the pepsin pass through unaffected. Typically, the chymosin is adsorbed on the affinity ligand in the column and later released by use of an eluting agent. However, the technique can be fine tuned such that under appropriate conditions the chymosin is not adsorbed but only retarded by the affinity ligand so that the pepsin is recovered first while an appropriate cut in the fractions separates the enzymes. This is accomplished by applying the calf rennet to the column at a pH of 5.5 (0.025 M citrate buffer) containing 0.5% (0.085 M) NaCl. In this embodiment chymosin will be retarded by the gel to a greater degree than pepsin so that pepsin will elute first followed by chymosin.

The blue dye affinity ligand described above is available commercially as Cibacron Blue F3GA in a form in which M is Na and R is Cl. This form of the dye is soluble and can be used to purify the rennet.

Other soluble forms of the dye, such as when R is polyethylene glycol, dextran or polyethyleneimine can be used in the purification of calf rennet in a similar manner. When R is polyethylene glycol, two-phase purification can be used. Two-phase purification involves the use of Cibacron blue derivatized polyethyleneglycol (CB-PEG) and dextran in water to form two phases. The upper phase will be rich in CB-PEG and the lower phase rich in dextran. The enzyme (chymosin) will complex with CB-PEG and stay in the upper phase. When the upper phase is separated and treated with salt (NaCl) there will be further separation into two phases. The enzyme will be released into aqueous (containing salt) phase. When R=dextran, the enzyme forms a blue dextranenzyme complex which can be separated on a gel filtration column. The enzyme can be dissociated from the complex with salt and rechromatographed to separate it from the blue dextran. With polyethyleneimine, the enzyme may form a precipitate or a complex which can be chromatographed further to separate the enzyme.

In a preferred method of practicing the present invention, the affinity ligand is immobilized by attaching it to a polymeric material so that in the foregoing formula R is agarose, Sephadex (dextran cross-linked with epichlorhydrin), polyacrylamide, agarose-polyacrylamide copolymer, cellulose, or even glass among other insoluble matrices. A particularly preferred insoluble affinity ligand is available as Blue agarose in which M in the above formula is Na and R is cross-linked agarose. Blue agarose has good flow properties as well as good mechanical and chemical stability. It is highly porous and the gel is known to be stable for years. These bead-like particles lend themselves readily for use in a conventional affinity gel chromatography column.

In the above formula, M can represent a monovalent or divalent cation such as $Li^+$, $Na^+$, $K^+$, $Rb^+$, $Ca^{++}$ or $Mg^{++}$. Depending on the coordination number of the $SO_3$ groups of the dye complexed to the metal, there can be excess negative or positive charge on the dye-metal ion complex if the cation is divalent. Typically the cation is $Na^+$.

When calf rennet containing approximately 15% pepsin is applied to a Cibacron Blue Agarose column at a pH of from 5.4 to 5.7 (preferably 5.5) in a low salt medium (0.025 M Na-citrate), pepsin passes through unadsorbed while chymosin is bound to the gel in the column. After washing the column with 0.025 M Na-citrate to remove unbound impurities, the chymosin can be eluted with 5% NaCl solution at pH 5.5 or with 50% (v/v) ethylene glycol −0.025 M citrate buffer at pH 6.0. The eluted chymosin was analyzed and found to contain greater than 97% pure chymosin. The material that passed through unadsorbed was found to contain greater than 96% pure pepsin. Thus a virtually complete separation of chymosin and pepsin is effected by this technique without having to destroy either enzyme. The separation appears to result from a combination of hydrophobic and electrostatic interactions of chymosin with Blue Agarose. It is unexpected that these two enzymes could be separated at pH 5.5 since they are both highly negatively charged at this pH.

The method of practicing the present invention is further illustrated by the following Examples:

EXAMPLE I

Five ml of calf rennet extract was dialyzed in one liter of 0.025 M citrate buffer at pH 5.5 with two changes of buffer overnight. The dialyzed sample was loaded onto a (1.5 cm×10 cm) column of Cibacron Blue Agarose (obtained from Pierce Chemical Co.) equilibrated with 0.025 M Na citrate buffer at pH 5.5 at a flow rate of 30 ml/hour. The column was then washed with the equilibrating buffer and the effluents monitored for absorbance at 280 nm and also for milk-clotting activity. When the activity returned to basal value, the bound enzyme was eluted by application of the 0.025 M citrate buffer (pH 5.5) containing 10% NaCl. The bound enzyme with milk-clotting activity eluted in a sharp peak as shown in FIG. 1. The fractions under A and B were pooled separately. The clotting activity of peak A was 23% of the total applied while that of peak B was 67% of the total applied activity. It was also found (by analysis on a DEAE cellulose column) that peak A was composed of 96% pepsin and peak B was 96.3% chymosin. Thus it was discovered that pepsin passed through the column unadsorbed while chymosin is bound and can be eluted with 10% NaCl. The clotting/proteolytic (C/P) ratios were 1.5, 10.8 and 5.9 for peak A, peak B and stock rennet, respectively which confirms the homogeneity of peaks A and B and the effectiveness of this technique for separating pepsin and chymosin.

In a variation of the elution pattern in this Example, 50% ethylene glycol 50% 0.025 M citrate buffer (v/v) at pH 6.2 was used to elute the bound chymosin with almost identical results. Elution of bound chymosin can thus be achieved by using either NaCl solution or a mixture of ethylene glycol and buffer. The clotting activity under the two peaks amounted to 90–95% of the initial applied activity.

EXAMPLE II

Five ml of rennet extract was dialyzed overnight in 0.025 M citrate buffer at pH 5.1 and applied to the blue gel column as in Example I at a flow rate of 30 ml/hour. The column was equilibrated with the same buffer. As before, the fraction which passed through the column had milk-clotting activity. After washing with equilibrating buffer, a gradient was applied with 0–18% NaCl in the buffer. The results are illustrated in FIG. 2. The passthrough fraction contained 20% of the clotting activity whereas the elution fraction contained 72%. Peak activity eluted at 3.17% NaCl and all clotting activity was completely eluted at 6.8% NaCl. Total recovery was 92% of which pepsin was 20% and chymosin 72%. Proteolytic activities of the two peaks were measured and the ratios of clotting to proteolytic activities were obtained. These are set out in Table I.

TABLE I

| Sample | Clotting[a] (%) (C) | Proteolytic Activity[b] (OD 280 nm/ml) (P) | C/P[c] |
|---|---|---|---|
| Stock Rennet | 33.2 | 11.1 | 3.0 |
| Peak B (top) | 22.4 | 2.0 | 11.2 |
| Peak A (top) | 3.7 | N.D. | N.D. |

N.D. = Not Determined
[a]Clotting activity is denoted in terms of percent strength by referring to the activity of a 50% Calf Rennet Standard.
[b]The values given are absorbance values at 280 nm per ml of the sample when incubated with hemoglobin substrate for 10 minutes. (For assay conditions refer to The Worthington Enzymes Manual).
[c]C/P is obtained by dividing percent strength clotting activity by the proteolytic activity (given as absorbance at 280 nm).

Although the proteolytic activity and the ratio C/P of peak A in the above case were not determined, in repeat experiments it was found that C/P ratio of peak A was about 1.0 to 1.5.

EXAMPLE III

Ten ml of calf rennet extract was dialyzed in 0.025 M Na citrate buffer at pH 5.5 containing 0.75 M Na$_2$SO$_4$. Nine ml of the dialyzed preparation (48% strength) was loaded on a Cibacron Blue Agarose column (1.5 cm × 10 cm) equilibrated with the same buffer containing 0.75 M Na$_2$SO$_4$ at a flow rate of 30 ml/hour. The column was washed with the equilibration buffer until absorbance at 280 nm and the clotting activity of effluents were close to zero. At this point the bound enzyme was eluted with 0.025 M Na citrate buffer containing 10% NaCl. The results of this work are represented in FIG. 3. The peak activity of chymosin was 52.33% which was higher than what was loaded indicating concentration of chymosin on the column. Recovery was 100%. The clotting and proteolytic activities of peaks A and B were compared with those of stock rennet. The results are set out in Table II.

TABLE II

| Sample | Clotting Activity (%) C | Proteolytic Activity (OD 280 nm/ml) P | C/P |
|---|---|---|---|
| Stock Rennet | 63.45 | 10.95 | 5.8 |
| Peak A | 6.9 | 7.67 | 0.9 |
| Peak B | 52.33 | 4.7 | 11.1 |

High C/P ratio indicates chymosin and low C/P ratio indicates pepsin. Once again the efficiency of separation is very good.

EXAMPLE IV

In order to evaluate the effectiveness of the separation of pepsin and chymosin under different initial salt concentrations, calf rennet was processed on the Cibacron Blue gel column at varying NaCl concentrations such as 1%, 2%, 3%, 10% and 18%. At all these salt concentrations chymosin and pepsin together pass through the column as a single peak unadsorbed at pH values in the range of 5.1-5.5. When an 0.5 M concentration of acetate, sulfate, citrate, or phosphate was used as the equilibrating and washing medium, pepsin and chymosin pass through the column one after the other. However, to separate the two effectively, a sharp cut in the effluent is necessary.

Subsequently, 5 ml of stock calf rennet was dialyzed in 0.025 M citrate buffer (pH 5.5) containing 0.5% NaCl (0.085 M), the column was equilibrated with the same medium, loaded with the dialyzed preparation and washed with the same buffer. As illustrated by FIG. 4, two peaks, A and B, appeared one after the other before any elution could be attempted. Further elution with 10% NaCl did not elute any milk clotting activity. Ninety-two percent of the applied activity was recovered. To determine if peaks A and B were really pepsin and chymosin, the proteolytic activities were determined on the two fractions connected by the dotted line in FIG. 4. Fraction 3 gave a C/P ratio of 1.7 while fraction 4 gave a ratio of 12.1 which is in line with previous identification of such fractions as pepsin and chymosin respectively. This embodiment, then, provides an effective alternative for separating the two fractions without having to bind either pepsin or chymosin on the column.

EXAMPLE V

Since it was shown in Example III that 0.75 M Na$_2$SO$_4$ is effective in separating pepsin and chymosin, the feasibility of a large scale preparation was further tested.

Rennet was extracted from calf stomachs using 10% Na$_2$SO$_4$ instead of the usual NaCl. The crude extract had a clotting activity of 14.5%. The extract was filtered through Whatman #1 filter paper and centrifuged for two hours at 10,000 rpm. The resulting supernatant had a clotting strength of 12.3%.

The conductivity of the extract was 46,300 ($\mu$S/cm). Eleven percent Na solution measured 60,800 $\mu$S/cm. So, in order to keep the Na$_2$SO$_4$ concentration at 0.77 M ($\approx$11%), additional Na$_2$SO$_4$ was added to 470 ml of the extract to bring the conductivity to 60,400 $\mu$S/cm ($\approx$11% Na$_2$SO$_4$). This was then ultrafiltered down to a volume of 250 ml. This 250 ml was processed on a wide Cibacron Blue gel column (6 cm × 14 cm) equilibrated with 11% Na$_2$SO$_4$ and 0.025 M Na citrate buffer at pH 5.5. The milk clotting activities of all the fractions (passthrough, wash and elution) were determined. The washing medium was the same as the equilibrium medium. Elution was effected by passing 5% NaCl through the gel.

The clotting activities of the fractions were plotted as a function of the fractions collected. They are shown in FIG. 5. The initial peak (a) represents the passthrough fraction containing 14% of the total applied clotting activity. The peak (b) represents the elution (5% NaCl) fraction which had 82% of the applied activity.

The proteolytic activities of the rennet applied to the column, the passthrough and the elution fractions were determined to test the efficacy of separation of pepsin and chymosin. Hemoglobin was used as the substrate. Essentially the proteolytic activity thus determined would show pepsin activity (since the pH was kept at 2.0). The proteolytic and clotting activities are given in Table III.

TABLE III

| Sample | Clotting Strength (%) (C) | Proteolytic Activity OD 280 nm per ml of Sample (P) | C/P |
| --- | --- | --- | --- |
| 1. Na$_2$SO$_4$ extracted rennet (concentrated) | 19.37% | 5.46 | 3.55 |
| 2. Pass-through fraction (Peak A) | 2.68% | 2.72 | 0.99 |
| 3. Elution fraction Peak B (top of the peak in figure) | 33.83% | 2.03 | 16.67 |
| 4. Sigma chymosin (1 mg/ml) | 18.29% | 1.87 | 9.78 |
| 5. Sigma pepsin (porcine) (1 mg/ml) | 26.90% | 23.93 | 1.12 |

As seen from the above Table, Sigma pepsin and chymosin have C/P values of 1.1 and 9.8, respectively. Our passthrough fraction and elution fraction give C/P values of 0.99 and 16.67, respectively, indicating that they are pure pepsin and pure chymosin, respectively.

Two hundred forty eight ml of 19.37% strength rennet was loaded. Two hundred ml of pepsin at a clotting strength of 2.68% and 250 ml of chymosin at an average strength of 15.65% were recovered. The peak concentration (peak B) of chymosin was, however, higher (33.83%) than the one loaded (19.37%), thereby indicating concentration of the enzyme by this technique. Recovery of total clotting activity in the two pools amounted to 93%.

What is claimed is:

1. A method for the purification of calf rennet which method comprises contacting the rennet with an affinity ligand of the formula:

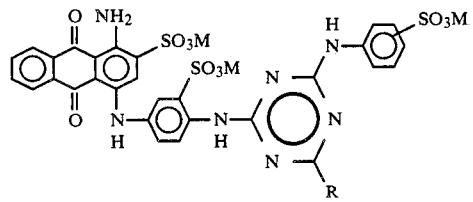

where R is a solubilizing moiety or a moiety which will insolubilize the ligand without affecting its affinity characteristics, at a pH of from 5.4 to 5.7 to cause separation of chymosin and pepsin contained in the calf rennet.

2. The method of claim 1 wherein the separation is carried out at a low ionic strength to cause selective retention of the chymosin by the affinity ligand.

3. The method of claim 1 wherein the rennet is passed through a column containing an insolubilized form of the affinity ligand in an admixture with NaCl at a concentration of about 0.085 M together with Na-Citrate in a concentration of about 0.025 M whereupon the flow of chymosin in the rennet is retarded relative to the flow of the pepsin to thereby cause the separation of these two enzymes.

4. The method of claim 1 wherein M is Na and R is Cl.

5. The method of claim 1 wherein R is polyethylene glycol, dextran or polyethyleneimine.

6. The method of claim 1 wherein R is agarose, dextran cross-linked with epichlorhydrin, polyacrylamide, an agarose-polyacrylamide copolymer, cellulose or glass.

7. The method of claim 1 wherein M is Na and R is cross-linked agarose.

8. The method of claim 1 wherein the pH is maintained at 5.5.

9. The method of claim 7 wherein the calf rennet is contacted with the affinity ligand in a chromatography column to cause the chymosin to become adsorbed thereto.

10. The method of claim 9 wherein the chymosin is eluted from the affinity ligand with a 5% NaCl solution at pH 5.5 or with a 50% (v/v) ethylene glycol-0.025 M citrate buffer solution at pH 6.0.

11. The method of claim 1 wherein the calf rennet is in the form of a 10% Na$_2$SO$_4$ extract from calf stomachs.

* * * * *